(12) United States Patent
Gilbard et al.

(10) Patent No.: US 9,050,288 B2
(45) Date of Patent: Jun. 9, 2015

(54) CLEANSER COMPOSITIONS AND METHODS FOR USING THE SAME

(71) Applicant: Advanced Vision Research, Inc., Woburn, MA (US)

(72) Inventors: Jeffrey Gilbard, Weston, MA (US); Yanick Douyon, Arlington, VA (US); Robert B Huson, Acton, MA (US)

(73) Assignee: ADVANCED VISION RESEARCH, INC., Woburn, MA (US)

( * ) Notice: Subject to any disclaimer, the term of this patent is extended or adjusted under 35 U.S.C. 154(b) by 0 days.

(21) Appl. No.: 14/528,420

(22) Filed: Oct. 30, 2014

(65) Prior Publication Data

US 2015/0057364 A1  Feb. 26, 2015

Related U.S. Application Data

(63) Continuation of application No. 13/871,133, filed on Apr. 26, 2013, which is a continuation of application No. 13/539,531, filed on Jul. 2, 2012, now Pat. No. 8,449,928, which is a continuation of application No. 12/771,246, filed on Apr. 30, 2010, now Pat. No. 8,231,912.

(60) Provisional application No. 61/174,628, filed on May 1, 2009.

(51) Int. Cl.
  *A01N 65/00* (2009.01)
  *A61K 31/122* (2006.01)
  *A61K 31/045* (2006.01)

(52) U.S. Cl.
  CPC ............. *A61K 31/122* (2013.01); *A61K 31/045* (2013.01)

(58) Field of Classification Search
  CPC ..................................................... A61K 36/61
  USPC ...................................................... 424/725
  See application file for complete search history.

(56) References Cited

U.S. PATENT DOCUMENTS

| | | | |
|---|---|---|---|
| 4,261,904 A | 4/1981 | Takeda et al. | |
| 5,009,890 A | 4/1991 | DiPippo | |
| 5,384,125 A | 1/1995 | DiPippo | |
| 6,585,961 B1 | 7/2003 | Stockel | |
| 7,485,327 B2 | 2/2009 | Kim et al. | |
| 8,231,912 B2 | 7/2012 | Gilbard et al. | |
| 8,449,928 B2 | 5/2013 | Gilbard et al. | |
| 2002/0173436 A1 | 11/2002 | Sonnenberg et al. | |
| 2003/0157138 A1 | 8/2003 | Eini et al. | |
| 2003/0161867 A1 | 8/2003 | Lu et al. | |
| 2005/0158405 A1 | 7/2005 | Boukas | |
| 2005/0220742 A1 | 10/2005 | Van Breen | |
| 2006/0057075 A1 | 3/2006 | Arkin et al. | |
| 2006/0068044 A1 | 3/2006 | Reynolds | |
| 2006/0275218 A1 | 12/2006 | Tamarkin et al. | |
| 2007/0003508 A1 | 1/2007 | Wooley et al. | |
| 2007/0243275 A1 | 10/2007 | Gilbard | |
| 2008/0241201 A1 | 10/2008 | Warr et al. | |
| 2010/0324151 A1 | 12/2010 | Gilbard | |
| 2012/0270953 A1 | 10/2012 | Gilbard et al. | |
| 2012/0288575 A1 | 11/2012 | Gilbard et al. | |

FOREIGN PATENT DOCUMENTS

| | | |
|---|---|---|
| EP | 095399 A2 | 10/1999 |
| EP | 2424374 | 3/2012 |
| EP | 2018103 | 8/2012 |
| FR | 2866564 A1 | 8/2005 |
| JP | 2002-037747 A | 2/2002 |
| RU | 2085204 C1 | 7/1997 |
| WO | 01-70215 A1 | 9/2001 |
| WO | 2006-119174 A1 | 11/2006 |
| WO | 2007-120817 A2 | 10/2007 |

OTHER PUBLICATIONS

Patent Cooperation Treaty, International Search Report issued on PCT/US2010/033140, mailed on Jun. 19, 2010, 3 pages.
Brand et al., tee tree oil reduces histamine-induces oedema in murine ears, Inflammation research: Official Journal of the European Histamine Research Society, Jun. 2002, vol. 51, No. 6, p. 233-289 (XP002688582).
European Search Report for EP 07 755402, issued Dec. 5, 2012, 3 pages.
Faran, et al., Tea tree oil: in vitro efficacy in otitis externa, The Journal of Laryngology and Otology, Mar. 2005, vol. 119, No. 3, p. 198-201 (XP9165425).
Naithani et al *Ocimum gratissimum, Ocimum canum* and *Ocimum kilimandscharicum*—a review, Journal of Medical and Aromatic Plant Sciences, 2002m vol. 24, p. 441-455.
Wikipedia, "Linalool", 3 pages, 2008.
Ezine artcles, 2009, 4 pages.
Kheirkhah et al., Corneal manifestations of ocular demodex infestation, American Journal of Opthalmology, May 2007, 743-749.
Patent Cooperation Treaty, International Search Report issued on PCT/US2007/009119, mailed on Jan. 7, 2008, 1 page.

*Primary Examiner* — Michael Meller
(74) *Attorney, Agent, or Firm* — Bryan Cave LLP

(57) ABSTRACT

The present invention is directed to anti-microbial cleanser compositions comprising linalool, hinokitiol and dipropylene glycol. The present invention further provides methods for using these compositions to maintain eyelid hygiene, to treat an ocular disorder or to clean a skin surface. The cleanser compositions of the present invention can be in the form of a foam, gel or liquid.

1 Claim, No Drawings

CLEANSER COMPOSITIONS AND METHODS FOR USING THE SAME

RELATED APPLICATIONS

This application claims the benefit of U.S. Provisional Application No. 61/174,628, filed May 1, 2009, the entire contents of which are hereby incorporated herein by reference.

BACKGROUND OF THE INVENTION

Numerous ophthalmologic diseases and disorders result from microbial overgrowth on the eyelid. The majority of these could be prevented or treated by using a product that has the ability to remove dirt and debris from the eyelid and surrounding area and, additionally, has the ability to kill microorganisms, e.g., bacteria or yeast, that colonize the area. Additionally, this product would have to be suitable for application to the eyelid and surrounding area.

Accordingly, the instant invention provides compositions and methods for cleaning the eyelid and/or skin surfaces.

SUMMARY OF THE INVENTION

The present invention is directed to novel compositions and methods effective for decreasing microbial colonization on the eyelid. The methods and compositions disclosed herein are useful for daily cleansing. These methods involve the easy and safe application of the composition to the eyelid in controlled doses effective for maintenance of eyelid hygiene. The disclosed compositions are effective against a broad range of microbes that commonly colonize the eye and surrounding tissue.

Accordingly, the invention provides cleanser compositions suitable for application to the skin and ocular surface comprising linalool, hinkokitiol and an alcohol. The alcohol can be a diol, such as a glycol. Exemplary glycols include propylene glycol, and ethylene glycol and dipropylene glycol.

The cleanser compositions of the invention may further comprise decyl glucoside, sodium trideceth sulfate, cocamidopropyl betaine, dipropylene glycol or mixtures thereof.

The cleanser compositions of the invention are suitable for direct application to the ocular surface, an eyelid or the skin surrounding the eyelid of a subject.

The cleanser compositions of the invention can be applied as a foam, gel or liquid.

In exemplary embodiments, the cleanser compositions of the invention are useful for the treatment of an ocular disorder, such as dry eye, excessive bacteria on the eyelid dermis, Meibomian gland dysfunction (MGD), blepharitis, acne rosacea, scalp dandruff, seborrheic dermatitis, chalazion, hordeolum, sty infectious conjunctivitis, corneal ulcer or any combination thereof. In specific embodiments, the ocular disorder is anterior or posterior blepharatis.

The cleanser compositions of the invention are effective against at least one of the following microorganisms: *S. aureus*, *P. aeruginosa*, *B. catarrhalis*, *E. coli*, *S. marcescens*, *S. epidermidis*, MRSA, and *P. ovale*. Specifically, the compositions are effective against antibiotic resistant bacteria such as methicillin resistant *S. aureus*.

Exemplified cleanser compositions of the invention contain the following components in approximately the following concentrations as a percent by weight:

| | | |
|---|---|---|
| (a) | Coladet BSB | 0.5-10.0%; |
| (b) | Decyl Glucoside | 0.2-10.0%; |
| (c) | Linalool | 0.5-2.0%; |
| (d) | Cocamidopropyl PG-Dimonium Choloride Phosphate | 0.01-5.0%; |
| (e) | Trisodium EDTA | 0.01-1.0%; |
| (f) | Allantoin | 0.01-1.0%; |
| (g) | Panthenol | 0.01-1.0%; |
| (h) | Hinokitiol | 0.01-5.0%; |
| (i) | Tea Tree Oil | 0.005-2.0%; |
| (j) | Vitamin E Acetate | 0.005-2.0%; |
| (k) | Water | 0.0-98.15%; |
| (l) | Dipropylene glycol | 1.0-50.0%; and |
| (m) | Cocamidopropyl betaine | 0.1-20.0%. |

A particular exemplified cleanser composition of the invention comprises the following components in approximately the following amounts as a percent by weight:

| | | |
|---|---|---|
| (a) | Coladet BSB | 3.8%; |
| (b) | Decyl Glucoside | 1.7% |
| (c) | Linalool | 0.9%; |
| (d) | Cocamidoproply PG-Dimonium Choloride Phosphate | 0.2%; |
| (e) | Trisodium EDTA | 0.1%; |
| (f) | Allantoin | 0.1%; |
| (g) | Panthenol | 0.1% |
| (h) | Hinokitiol | 0.05%; |
| (i) | Tea Tree Oil | 0.025%; |
| (j) | Vitamin E Acetate | 0.01%; |
| (k) | Water | 68.215%; |
| (l) | Dipropylene glycol | 23.0%; and |
| (m) | Cocamidopropyl betaine | 2.0%. |

Another specific composition of the invention is an ophthalmologically acceptable cleanser composition comprising linalool, hinkokitiol and cocamidopropyl PG-dimonium chloride phosphate.

The cleanser compositions of the invention are in the pH range from about 4.5 to about 6.0, specifically from about 5.3 to about 5.7.

The invention also provides methods of cleaning a body surface of a subject by providing the cleanser composition described herein and applying the cleanser composition to the surface; thereby cleaning the surface.

The invention also provides methods of cleaning a body surface of a subject by providing a dispensing device containing the cleanser composition described herein, dispensing an amount of the cleanser composition from the dispensing device; and applying the foam to the surface, thereby cleaning the surface.

In some methods, the compositions are in the form of a foam, gel or liquid. In other methods, the surface being treated is an eyelid.

The invention further provides methods of treating a subject having a *demodex* infestation, by applying a cleanser composition of the invention to the eye lid, thereby treating the *demodex* infestation.

In the methods of the invention, the cleanser composition is formulated such that upon application to the body surface or eyelid, the cleanser composition does not substantially damage or irritate the body surface or eyelid.

In an exemplary method of the invention, the inventions provides a method of treating ocular disorder in a subject by providing a dispensing device containing the cleanser compositions described herein, dispensing an amount of the cleanser composition from the dispensing device in the form of foam, liquid or gel, and applying the composition to the eye lid, thereby treating an ocular disorder. The method may further comprise cleansing the eyelid by localized and sustained massaging of the composition.

The disclosed methods are useful for the treatment of, for example, dry eye, excessive bacterial colonization on the eyelid, Meibomian gland dysfunction (MGD), blepharitis, acne rosacea, scalp dandruff, seborrheic dermatitis, chalazion, hordeolum, sty, infectious conjunctivitis, corneal ulcer, *demodex* infestation, or any combination thereof. In specific exemplary methods, the oclar disorder is anterior blepharatis or posterior blepharitis.

The invention also provides devices for producing foam, wherein the device contains a cleanser composition suitable for application to the skin comprising linalool, hinokitiol and dipropylene glycol. In exemplary embodiments of the invention, the cleanser composition is dispensed utilizing a device having a pump mechanism and a squeeze mechanism and wherein the device delivers the foam to an applicator for application to the eyelid of the subject.

The invention also provides kits for maintaining eyelid hygiene in a subject comprising the cleanser composition of the invention or the devices comprising the cleanser compositions, and instructions for use. The kits can further include an applicator, such as a sponge.

DETAILED DESCRIPTION OF THE INVENTION

As described herein, the inventors have invented highly effective compositions for cleansing the eye and the surrounding area, and for treating ocular disorders. The inventors also set forth methods and kits for using these cleanser compositions.

Definitions

The invention will be described with reference to the following definitions that, for convenience, are collected here.

The term "controlled concentration" is defined as a characteristic of a mixture where the ratio of active ingredient(s) to non-active ingredient(s) is controllable at a prescribed level, and therefore definitive amounts of the mixture, and ingredients contained therein, can be delivered/distributed. Such a characteristic is useful in providing controllable dosage regimens (i.e., improving predictability of the dose delivered).

The term "foam" is defined as a mass of bubbles of air or gas in a matrix of liquid, such as the compositions described herein. Foam can be generated by any of the various methods know in the art.

The term "cleaning an eyelid" is used herein to describe the act of significantly reducing the amount of microbes, dirt, debris, or otherwise undesired material from the eyelid and/or the area around the eye. In exemplary embodiments, the invention provides methods for cleansing the eye and surrounding areas and decreasing the colonization of *S. aureus, P. aeruginosa, B. catarrhalis, E. coli, S. marcescens, S. epidermidis*, and *P. ovale*. In one embodiment, the *S. aureus* are methicillin resistant *S. aureus*.

The term "direct application" is used herein to describe the application of a cleanser composition to a subject, e.g., an eyelid or a surface, e.g., the skin, of a subject, with no additional processing or preparation of the cleanser, e.g., no manual foaming or lathering, prior to application.

The term "dispensing" is defined as the act of delivering a cleanser composition to an applicator that has not been stored in direct contact with an applicator, e.g., in contrast to commercially available eyelid scrubs where the sponge is stored in direct contact with the cleanser liquid.

The term "dry eye" is known in the art as a condition of a subject that has a lack of quality and/or quantity of tears. Dry eye is often an age-related disease. Meibomian gland dysfunction is a frequent cause of dry eye and manifests itself in such forms as stenosis or closure of the meibomian gland orifices, inflammation of the meibomian glands, sty, hordeolum or other inflammation of the connective tissue. Meibomian gland dysfunction is commonly linked with ocular rosacea, blepharitis, and other inflammation of the eyelids. All of these causes of inflammations of the skin are related to bacterial or yeast infection.

The term "eyelid" as used herein, includes the ocular surface most commonly the ocular surface, both the interior and exterior surfaces of the eyelid, the eyelid margin, the glands in and around the eyelid margins, the hair follicles of the eye, the eyelashes, and the periocular skin surrounding the eye.

The term "ocular disorder" is defined as a disorder of the eye that can be treated or improved by cleansing the eyelids and/or eye of microbes and/or debris. Exemplary ocular disorders include, but are not limited to, dry eye, excessive bacteria on the eyelid dermis linked to Meibomian gland dysfunction (MGD), blepharitis, acne rosacea, scalp dandruff, seborrheic dermatitis, chalazion, hordeolum, sty, infectious conjunctivitis, corneal ulcers and any combination thereof.

The term "localized and sustained massaging", as used herein, defines a manner of agitation of an eyelid of a subject. The massaging is focused on the eyelid for an amount of time sufficient for cleaning an eyelid and surrounding areas, and results in significant agitation of the glands of the eyelid. This term is distinguishable from the incidental agitation of the eyelid associated with, for example, washing the entire face including the eyelid. In certain embodiments, the massaging is sustained for at least 5 seconds and possible for 30-60 seconds.

The term "sponge" as used herein includes all absorbent materials such as pads, swabs, tissues, Q-tips, washcloths, or fiber applicators of any kind that may be used to induce foaming and/or used as an applicator for an eyelid cleanser.

The term "transiently stable foam" is used herein to define a foam that maintains its foam nature for a sufficient amount of time as to be useful in the application to an eyelid of a subject. A transiently stable foam need not be present in the form of a foam indefinitely, but rather only as long as needed to provide a subject sufficient time to apply the dispensed foam to the eyelid.

The term "treatment" as used herein is defined as prophylactic treatment (e.g., daily preventative use) or therapeutic treatment (e.g., a single treatment or a course of treatment) of a subject with an ocular disorder, which results in the reduction, alleviation, or elimination of at least one symptom of an ocular disorder.

Methods and Compositions

Decreasing microbial overgrowth on the eyelids and surrounding tissues is important for treating dry eye, blepharitis and for prophylaxis of infection prior to eye surgery. Patients with dry eye and blepharitis have microbial overgrowth on the eyelid skin. As such, the present invention is intended to emphasize the maintenance of eyelid hygiene through prophylaxis in addition to treatment using the compositions and methods of the present invention. The present methods, which involve localized and sustained massaging of the eyelids, assist in the removal of any overgrowth of common bacteria and yeast that cause inflammation of the eyelids and meibomian glands and pose a risk for those having surgery.

Accordingly, the invention provides cleanser compositions that are suitable for direct application to an eyelid, or surrounding area, of a subject that are effective for maintaining eyelid hygiene. The cleanser composition may be specifically formulated for the treatment of an ocular disorder, e.g., an ocular disorder selected from those including dry eye, excess bacteria on the eyelid dermis linked to Meibomian gland dysfunction (MGD), blepharitis, acne rosacea, scalp dandruff, seborrheic dermatitis, chalazion, hordeolum, sty or any combination thereof.

The cleanser compositions of the invention can also be used to clean other skin surfaces, e.g., the hands or feet.

The cleanser compositions of the invention contain linalool, hinokitiol and an alcohol, e.g., a diol such as glycol, e.g. diproplyene glycol.

More specifically, the cleanser compositions may contain one of more of the following components: linalool, hinokitiol, coladet BSB, decyl glucoside, cocamidopropyl PG-dimonium chloride phosphate, cocamidopropyl betaine, trisodium ethylenediaminetetraacetic acid (trisodium EDTA), allantoin, panthenol, *melaleuca alternifolia* (Tea Tree) leaf oil, vitamin E acetate, citric acid, dipropylene glycol, and sodium hydroxide.

Linalool is a naturally occurring terpene alcohol with broad spectrum antimicrobial properties. It has limited solubility in water and, therefore, a solubilizer must be added to increase the antimicrobial activity of linalool. Suitable solubilizers include diol alcohols such as, for example, ethylene glycol, propylene glycol, dipropylene glycol. In exemplary embodiments of the invention, the cleanser compositions comprise between about 0.5 to about 2.0% linalool, between about 0.7 and about 1.5% linalool or preferably about 0.9% linalool.

Hinokitiol is a tropolone alcohol with antimicrobial and antifungal activity. It is particularly effective against the scalp dandruff or *P. Ovale* that is common in patients with seborrheic blepharitis. In exemplary embodiments of the invention, the cleanser compositions comprise between about 0.01 and about 5.0% hinokitiol, or between about 0.02 and about 3.0% hinokitiol, or preferably about 0.05% hinokitiol.

Coladet BSB is surfactant blend intended to deliver very mild, gentle foaming activity and is available from Colonical Chemical (Dalton, Ga.). When combined with decyl glucoside and cocamidopropyl betaine the solution forms thick, dense and gentle foam. In exemplary embodiments of the invention, the cleanser compositions comprise between about 0.5 and about 10.0% coladet BSB, between about 0.7 and about 7.0% coladet BSB, and preferably about 3.6% coladet BSB.

Decyl glucoside is a mild non-ionic surfactant. When used in combination with coladet BSB and cocamidopropyl betaine it results in improved foaming characteristics to create fuller, denser and thicker foam. In exemplary embodiments of the invention, the cleanser compositions comprise between about 0.2 and about 10% decyl glucoside, between about 0.5 and about 4% decyl glucoside and preferably about 1.7% decyl glucoside.

Cola® Lipid C, chemically described as cocamidopropyl PG-dimonium chloride phosphate, is a coconut oil derived phospholipid composed predominantly of diester and triester phosphatides with multiple chain groups. In addition to topically simulating the properties displayed by the polar stratum corneum lipids, Cola® Lipid C displays a broad range of functional attributes including gentle cleansing and foaming properties, anti-irritation effects when combined with anionic surfactants, unusually high substantivity, and long lasting skin conditioning, Cola® Lipid C is non-irritating to skin and eyes. In exemplary embodiments of the invention, the cleanser compositions comprise between about 0.01% and about 5% cocamidopropyl PG-dimonium chloride phosphate, between about 0.1 and about 4% cocamidopropyl PG-dimonium chloride phosphate, or preferably about 0.2% cocamidopropyl PG-dimonium chloride phosphate.

Cocamidopropyl betaine is used as foam booster stabilizer to provide improved foaming characteristics. Tegobetaine is a 35% minimum active solution of cocamidopropyl betaine. Other betaines, e.g., sultaines, may also be used. In exemplary embodiments of the invention, the cleanser compositions comprise between about 0.1 and about 20% cocamidopropyl betaine, between about 0.5 to about 10% cocamidopropyl betaine or preferably about 2.0% cocamidopropyl betaine.

Trisodium ethylenediaminetetraacetic acid (EDTA) is. Other protonated forms EDTA may be substituted for trisodium EDTA. In exemplary embodiments of the invention, the cleanser compositions comprise between about 0.01 to about 1.0% trisodium EDTA, between about 0.2 to about 0.7% trisodium EDTA or preferably about 0.1% trisodium EDTA.

Allantoin is used as a skin healer. It increases the smoothness of the skin; promotion of cell proliferation and wound healing; and has a soothing, anti-irritant, and skin protectant effect by forming complexes with irritant and sensitizing agents. In exemplary embodiments of the invention, the cleanser compositions comprise between about 0.01 to about 1.0% allantoin, about 0.05 to about 0.7% allantoin, or preferably about 0.1% allantoin.

Panthenol is the alcohol analog of pantothenic acid (vitamin B5). Panthenol functions as a moisturizer, humectants and emollient. Panthenol (dL panthenol) improves hydration, reduces itching and inflammation of the skin and accelerates and improves healing of epidermal wounds. In exemplary embodiments of the invention, the cleanser compositions comprise between about 0.01 to about 1.0% panthenol, about 0.05 to about 0.7% panthenol, or preferably about 0.1% panthenol.

*Melaleuca Alternifolia* (Tea Tree) leaf oil is a natural antifungal and antibacterial composition. It is effective against nail fungus, ringworm, athlete's foot, dandruff, acne and many types of infestations including lice, mites and scabies. Tea tree oil is not just soothing and disinfecting, it is capable of penetrating into the lower skin layers with its anti-inflammatory, disinfectant, pain killing and wound healing qualities. In exemplary embodiments of the invention, the cleanser compositions comprise between about 0.005 and 2.0% *Melaleuca Alternifolia* (Tea Tree) leaf oil, and preferably about 0.025% *Melaleuca Alternifolia* (Tea Tree) leaf oil.

Vitamin E acetate is an antioxidant, possessing the ability to increase the moisturization of the skin. In addition to the properties related to skin moisturization and maintenance, vitamin E acetate is also antioxidant to linalool. In exemplary embodiments of the invention, the cleanser compositions comprise between about 0.005 and about 1.0% vitamin E acetate, between about 0.008 and about 0.5% vitamin E acetate, or preferably about 0.01% vitamin E acetate.

Dipropylene Glycol (DPG LO+) provides excellent co-solvency for water, oils and hydrocarbons, with minimal odor, low skin irritation potential, low toxicity and consistent isomer distribution, making it ideal for use in pharmaceutical and personal care products. Other low diols such as propylene glycol and ethylene glycol may be used. In exemplary embodiments of the invention, the cleanser compositions comprise between about 1 and about 50% dipropylene glycol, between about 5 and about 40% dipropylene glycol or preferably about 23.0% dipropylene glycol.

Acids and bases, such as citric acid and sodium hydroxide can be used to adjust the pH of the composition to the desired range, e.g., near the physiologic pH of the skin, 4.5-6.0 or preferably 5.3-5.7.

In exemplary embodiments, the invention provides a opthophthalmologically acceptable cleanser composition comprising the following components in the following range of concentrations:

| (a) | Coladet BSB | 0.0-10.0%; |
|---|---|---|
| (b) | Decyl Glucoside | 0.2-10.0%; |
| (c) | Linalool | 0.5-2.0%; |
| (d) | Cocamidoproply PG-Dimonium Choloride Phosphate | 0.01-5.0%; |
| (e) | Trisodium EDTA | 0.01-1.0%; |
| (f) | Allantoin | 0.01-1.0%; |
| (g) | Panthenol | 0.01-1.0%; |
| (h) | Hinokitiol | 0.01-5.0%; |
| (i) | Tea Tree Oil | 0.005-2.0%; |
| (j) | Vitamin E Acetate | 0.005-2.0%; |
| (k) | Water | 0.0-98.15%; |
| (l) | Dipropylene Glycol | 1.0-50.0%; and |
| (m) | Cocamidopropyl Betaine | 0.1-20.0%; |

In a further exemplary embodiment, the invention provides a opthophthalmologically acceptable cleanser composition comprising the following components at about the following concentrations:

| (a) | Coladet BSB | 3.6%; |
|---|---|---|
| (b) | Decyl Glucoside | 1.7%; |
| (c) | Linalool | 0.9%; |
| (d) | Cocamidopropyl PG-Dimonium Choloride Phosphate | 0.2%; |
| (e) | Trisodium EDTA | 0.1%; |
| (f) | Allantoin | 0.1%; |
| (g) | Panthenol | 0.1% |
| (h) | Hinokitiol | 0.05%; |
| (i) | Tea Tree Oil | 0.025%; |
| (j) | Vitamin E Acetate | 0.01%; |
| (k) | Water | 68.215%; |
| (l) | Dipropylene Glycol | 23.0%; and |
| (m) | Cocamidopropyl Betaine | 2.0% |

The invention is further directed to a method of cleaning an eyelid of a subject or to treat ocular disorder in a subject. The method comprises the steps of providing a cleanser composition, dispensing the cleanser composition, applying the composition to the eyelid, and, optionally, agitating the eyelid by localized and sustained massage of the composition onto the eyelid. The composition maybe dispensed onto a fingertip or an applicator device such as a sponge. The subject in need of treatment may have been diagnosed previously with an ocular disorder.

The invention is further directed to a method of cleaning a surface, e.g., skin surface, e.g. a skin surface, of a subject. The method comprises the steps of providing a cleanser composition, dispensing the cleanser composition; applying the composition to the surface and optionally agitating the surface. The composition maybe dispensed onto a fingertip or an applicator device such as a sponge. The subject in need of treatment my have been diagnosed previously with an ocular disorder.

The invention also provides methods of cleaning the eyelid using the cleanser composition in the form of a foam. The method comprises the steps of providing a cleanser composition, dispensing the cleanser composition in the form of a foam, applying the foam to the eyelid, and, optionally, agitating the eyelid by localized and sustained massage of the foam onto the eyelid. The foam maybe dispensed onto a fingertip and the fingertip is used to agitate the eyelid. The subject in need of treatment may have been diagnosed previously with an ocular disorder.

Furthermore, the dispensing apparatus may deliver foam to an applicator, e.g., a finger, utilizing a pump mechanism or a squeeze mechanism. It would also be understood by the ordinarily skilled artisan that the methods described above may utilize the foam in combination with any mechanical cleaning technique, for example, commercially available eyelid pads or scrubs.

The cleanser composition of the invention may be in the form of a liquid, gel or a foam. The cleanser composition may be any aqueous solution that can be formulated to form, provided that the composition is not significantly deleterious to the comfort or health of the eye and/or detracts from the compliance of use. For example, the cleanser composition may be an aqueous formulation formulated with sufficient additives to produce a stable foam from a dispenser engineered to produce a foam.

In certain embodiments of the invention, the cleanser composition can be dispensed from a dispensing apparatus. In one embodiment, the dispensing apparatus can be any device that delivers a cleanser composition in the form of a foam. However, it should be understood that, in contrast to commercially available eyelid scrubs where the sponge is stored in direct contact with the cleanser liquid, a dispenser useful in the methods of the invention is one in which the cleanser composition, e.g., cleanser composition of the present invention, is not stored in direct contact with an applicator. For example, the dispensing apparatus may be a device that has a container portion for containing the liquid cleanser composition (or liquid cleaning agent and a separately contained aqueous portion), an induction spout that acts to thaw the liquid cleanser from the container upon actuation, and a foaming portion attached to the induction spout that creates a controlled concentration foam from the liquid composition received from the induction spout. The induction spout may be actuated by a pump or a squeeze mechanism. A preferred dispenser is an airless foamer, e.g. a mini-airless foamer.

The cleanser compositions of the invention may include any aqueous solution that contains surfactants or additives with surfactant-like behavior The compositions of the invention may be used one or more time per day, or as directed by a doctor.

The cleanser compositions may be formulated so that application to the eyelid does not substantially damage the skin of the eyelid, even with frequent, e.g., twice daily, application. Furthermore, the cleanser compositions of the invention may be formulated for any desired property, e.g., substantially non-irritating, maintenance of pH of the eyelid skin, improved ability to remove dirt and debris, and/or to increase the stability of the controlled concentration foam.

The cleanser can be formulated as a liquid, gel or foam. The liquid form may be added with a moistened pad or sponge. The gel form can be applied with a pad or sponge as well as delivered with the fingers. The gel has the advantage that it will not drain between the fingers.

The foam form may be prepared by generating a foam from an aqueous solution that contains sufficient additives, e.g., surfactants or additives with surfactant-like behavior, to produce a foam that is stable. The foam provides a standardized, substantially invariable, and predefined amount of cleaning agent in a given amount of foam thus, improving the dosing regimen for maintaining eyelid hygiene. Moreover, once generated, the foam is suitable for application directly to the eyelid of subject, with the fingers, with the advantage that it does not drain between the fingers as a liquid with the advantage that the dose of the cleaning agent is well-defined, i.e., controlled, to assist in the process of accurate prescription. Additionally, the chosen dilution ratio may be customized based on the desired application, i.e., more concentrated for applications that require increased/enhanced cleaning.

The foam should be transiently stable in order to be useful. The foam need not be present in the form of a foam indefinitely; rather, the foam needs to be stable only as long as needed to provide a subject sufficient time to apply the dispensed foam to the eyelid. The stable foam is useful in gently removing dirt and debris from the eyelid and penetrating between the eyelashes and into the hair follicle, which are known to catch debris. Additionally, a stable foam which is applied independent of a sponge applicator contributes to the improved effectiveness of the present invention by introducing the step of massaging the eyelid with the fingers, which is more beneficial for the maintenance of skin integrity than the use of abrasive scrubbing.

Application of the composition to the eyelid or a surface of a subject may be by self-administration or by a trained professional, e.g., a doctor. More importantly, the application of the composition may be direct; e.g., it may be applied with a fingertip directly to the eyelids for blepharitis or to the ocular surface for the treatment of an infectious conjunctivitis or corneal ulcer.

In contrast to known methods which involve manual foaming or lathering, either with or without the agitation of a sponge, the foam present invention requires no additional processing or preparation of the cleanser prior to application to the eyelid. The advantage of eliminating this processing step ensures the presence of a standardized amount of cleaning agent in the resulting foam, i.e., the use of a controlled concentration foam.

Agitating the eyelid of surface by localized and sustained massaging of the composition improves the removal of dirt and debris as compared with known methods. Massaging is sustained for a period of time sufficient to substantially stimulate the cleaning of the eye or surface. For example, the massaging may be maintained for at least 5-60 seconds.

The method of cleaning an eyelid or surface may further include a rinsing step. This step preferably comprises a simple water rinse. The composition may be rinsed with ample water after application and massage by bringing ample water to eyelid and eyelashes, e.g., with a hand, finger or any container suitable for this purpose.

The methods of the invention are not meant to only work in isolation. The method of cleaning may also include a wiping step in lieu of rinsing step. The composition may be wiped off with a clean tissue, for example. More particularly, this invention provides a kit containing a product useful for cleaning an eyelid, optionally packaged with additional instructions for use in maintaining eyelid hygiene or treating an ocular disorder in conjunction with the kits of the present invention.

The methods and compositions of the invention find numerous commercial applications that could beneficially utilize the methods and compositions for eyelid hygiene, treatment or prevention or ocular disorders, or cleansing of a surface, e.g., a skin surface. Consequently, the invention includes a kit comprising a cleanser composition of the invention and instructions for use. In one embodiment, the kit includes a dispenser that is capable of generating a foam The kit may further comprise an applicator, e.g., a sponge.

EXEMPLIFICATION OF THE INVENTION

The present invention may be further illustrated by the following non-limiting examples.

Example 1

An Exemplary Formulation of the Invention

| Ingredients (INCI) | Weight % |
|---|---|
| Purified Water | 68.215 |
| Dipropylene Glycol | 23.0 |
| Cocamidopropyl Betaine | 2.0 |
| Coladet BSB | 3.6 |
| (Blend of mild surfactants-Peg-80 Sorbitan Laurate, Sodium Trideceth Sulfate, Cocamidopropyl Betaine Sodium Lauroamphoacetate, PEG-150 Distearate, Sodium Laureth-13 Carboxylate) | |
| Decyl Glucoside | 1.7 |
| Linalool | 0.9 |
| Cocamidopropyl PG-Dimonium Chloride Phosphate | 0.2 |
| Trisodium EDTA | 0.1 |
| Allantoin | 0.1 |
| Panthenol | 0.1 |
| Hinokitiol | 0.05 |
| Melaleuca Alternifolia (Tea Tree) Leaf Oil | 0.025 |
| Vitamin E Acetate | 0.01 |
| Citric Acid | 0.1 (max if needed for pH adjust.) |
| Sodium Hydroxide | 0.2 (max if needed for pH adjust) |

Protocol for Manufacturing

The above compositions were made in the following manner Each component was individually added to a vessel containing water at room temperature and mixed until uniform. If needed, the formulas are adjusted to physiological skin pH with citric acid or sodium hydroxide. The resulting preparation is a clear, single phase solution. Each preparation was prepared in this same manner. The component amounts given in the tables are expressed as percent by weight.

Experimental Design

A suspension of bacterial cells was exposed to the test substance for specified contact times. After exposure, an aliquot of the suspension was transferred to a neutralizing structure media and assayed for survivors. Appropriate purity, subculture medium sterility, microorganism population and neutralization controls were performed.

Test Exposure: 30 seconds and 60 seconds

Exposure Temperature: Room temperature (21.0-23 C.)

Soil Load Description: No Organic soil load

Dilution: Ready to Use (RTU)

Recovery Media:

Neutralizing Subculture Medium: Letheen Broth+2.0% Lecithin+2.0% Tween 80

Efficacy Data

| Test Organism | Exposure Time | Test Population Control (CFU/mL)* $Log_{10}$ | Number of Survivors (CFU/mL)* | $Log_{10}$ Number of Survivors | Percent Reduction | $Log_{10}$ Reduction |
|---|---|---|---|---|---|---|
| Staphylococcus aureus | 30 seconds | $9.4 \times 10^5$ | $2.39 \times 10^4$ | 4.378 | 97.5% | 1.59 |
| | 60 seconds | 5.97 | $9.0 \times 10^3$ | 3.95 | 99.0% | 2.02 |
| Pseudomonas aeruginosa | 30 seconds | $3.8 \times 10^6$ | <2 | <0.3 | >99.9999% | >6.3 |
| | 60 seconds | 6.58 | <2 | <0.3 | >99.9999% | >6.3 |
| Moraxella (Branhamella) catanhalis | 30 seconds | $1.45 \times 10^6$ | <2 | <0.3 | >99.99% | >4.9 |
| | 60 seconds | 5.161 | <2 | <0.3 | >99.99% | >4.9 |
| Escherichia coli | 30 seconds | $5.0 \times 10^5$ | <2 | <0.3 | >99.999% | >5.4 |
| | 60 seconds | 5.70 | <2 | <0.3 | >99.999% | >5.4 |
| Serratia marcescens | 30 seconds | $1.48 \times 10^6$ | $1.1 \times 10^2$ | 2.04 | 99.99% | 4.13 |
| | 60 seconds | 6.170 | <2 | <0.3 | >99.999% | >5.9 |
| Staphylococcus epidermidis | 30 seconds | $8.1 \times 10^5$ | $6.5 \times 10^3$ | 3.81 | 99.2% | 2.10 |
| | 60 seconds | 5.91 | $2.05 \times 10^3$ | 3.312 | 99.7% | 2.60 |
| Staphylococcus aureus-MRSA | 30 seconds | $1.53 \times 10^6$ | $2.04 \times 10^2$ | 2.310 | 99.9% | 3.875 |
| | 60 seconds | 6.185 | $4.8 \times 10^1$ | 1.68 | 99.99% | 4.51 |
| Pityrosporum ovale | 30 seconds | $3.1 \times 10^3$ | $4.24 \times 10^2$ | 2.627 | 86.3% | 0.86 |
| | 60 seconds | 3.49 | $1.3 \times 10^2$ | 2.11 | 96.8% | 1.38 |

*colony forming units per mL of test mixture

Example 2

Efficacy of Formulations Against *Demodex* Mites

The goal of this example was to determine if the formulations of the invention are effective for killing *Demodex* mites.

Materials. Control 50% baby shampoo, 5% Formula as Set forth in Example 1, 5% Tea Tree Oil (TTO), 50% TTO Methods. Patients who exhibited cylindrical sleeves on their lashes were selected and a slit lamp exam was performed to determine which lashes would be epilated. The lashes were then immersed in an agent and examined with a light microscope. The presence of *Demodex* was determined and the amount of time for the agent to completely kill the *Demodex* mite was noted. Kill time was determined by the cessation of leg movements of the mites for a period of 10 minutes.

Results. *Demodex* survived for more than 180 minutes in 50% baby shampoo. In contrast, the mean survival time for *Demodex* immersed in 50% TTO, 5% TTO, and the formulation set forth in Example 1 ranged from 8 minutes (50% TTO) to 51 minutes (formulation set forth in Example 1).

Anterior blepharitis is an inflammation of the eyelids that causes redness, irritation, an itchy sensation, and the formation of dandruff-like scales on eyelashes. It involves the irritation of the outer front edge of the eyelid where the eyelashes are attached. Many causes of anterior blepharitis have been described, but this study is particularly concerned with ocular *Demodex* infestation.

Patients with anterior blepharitis often present with cylindrical dandruff on their eyelashes. Cylindrical dandruff (CD) are scales that form clear cuff collars around eyelash roots. This is often indicative of the presence of ocular *Demodex* because it is regarded as pathognomonic of *Demodex* infestation.

Materials
  50% Johnson and Johnson baby shampoo
  5% Tea Tree Oil (TTO)
  the formulation set forth in Example 1

Methods

Patients were selected, who displayed evidence of anterior blepharitis. A slit lamp was used to examine the patient population to determine that those selected evinced cylindrical dandruff around at least 8 eyelashes. Based on previous studies, cylindrical dandruff on 8 eyelashes is sufficient to indicate a modest infestation of ocular *Demodex*. The patient selection was not exclusive based on age, ethnicity, or gender. The only patients excluded from the study were those who were currently on a tea tree oil treatment regimen or those who had undergone fluorescent staining.

One affected eyelash from each fourth of the upper eyelids was epilated using jeweler's type forceps and a slit lamp microscope (Nikon, DiaScope II, Japan).

Two individual eyelashes were placed on each microscope slide and immediately saturated with 20 μL, of a blindly selected test solution. A plastic coverslip was then placed over the mixture and the slide was examined. Under the microscope, we searched for the presence of living adult *Demodex*.

Confirmation of the mites' live status was evidenced by vigorous movement of their four pairs of legs. Adult *Demodex* is distinguishable from juvenile *Demodex* because of its well formed legs, stumpy body, and length of approximately 0.4 mm.

Once the determination was made that mites were present and alive on the slides, mitesw were observed every 10 minutes to check for obvious signs of reduction of leg movement. When it became apparent that only one of its legs was moving irregularly, the mite under observation was watched continuously until its leg ceased to move.

Observation was continued for a period of 10 additional minutes following the cessation of leg movement in order to establish the accuracy of our recorded kill time. Kill time is calculated as the time between exposure of the mite to the agent and cessation of mite leg movement for a period longer than 10 minutes.

Solutions in which *Demodex* immersion did not result in death after 180 minutes were assumed to be ineffective and observation was discontinued. *Demodex* were excluded from the study if they did not have vigorous leg movements at the beginning of observation, or if more than half of their bodies were encased in cylindrical dandruff.

Results

TABLE 1

Resultant mean kill time of the test agents that
successfully killed the *Demodex* before 180 minutes

|  | 50% Baby Shampoo | 5% TTO | Formulation of Example 1 |
|---|---|---|---|
| Mean kill time (minutes) | >180 | 14.000 | 51.429 |
| # of *Demodex* | 20 | 17 | 21 |

Discussion

In this in vitro study of the effects of applying topical and eyelid cleansing agents to *Demodex* derived from patients with anterior blepharitis, it was determined that only 5% TTO and the formulation set forth in Example 1 were effective in eradicating the mites in a timely manner. 50% TTO was able to kill the *Demodex* in approximately 8 (5.6) minutes, 5% TTO in 14 (7.3) minutes, and the formulation set forth in Example 1 in 51 (25.7) minutes. 50% baby shampoo was unable to kill mites within a period of 180 minutes.

Although it is understood that TTO is a very effective cleansing agent, its use among patient populations may not be as high as expected because TTO acts as an irritant if it enters a patient's eyes.

Accordingly, the formulation set forth in Example 1 is effective for treating subjects having a *demodex* infestation of the eye.

What is claimed is:

1. A cleansing product comprising a sponge applicator and an aqueous cleansing composition added to the sponge applicator, the aqueous cleansing composition comprising 0.5 wt % to 2 wt % linalool, 0.01 wt % to 5 wt % hinokitiol, 1 wt % to 50 wt % dipropylene glycol, 0.1 to about 20 wt % cocamidopropyl betaine, 0.005 to 2.0 wt. % tea tree oil, 0.01 to 5 wt % cocamidopropyl PG-dimonium chloride phosphate, 0.01 to 1.0 wt % EDTA, 0.005 to 1.0 wt % Vitamin E acetate, 0.01 to 1.0 wt % allantoin, 0.01 to 1.0 wt % panthenol, and 0.2 to 10 wt % decyl glucoside.

* * * * *